United States Patent [19]

Schroeppel

[11] Patent Number: 4,545,380
[45] Date of Patent: Oct. 8, 1985

[54] METHOD AND APPARATUS FOR SETTING AND CHANGING PARAMETERS OR FUNCTIONS OF AN IMPLANTED DEVICE

[75] Inventor: Edward A. Schroeppel, Miramar, Fla.

[73] Assignee: Cordis Corporation, Miami, Fla.

[21] Appl. No.: 601,807

[22] Filed: Apr. 16, 1984

[51] Int. Cl.⁴ .............................................. A61N 1/08
[52] U.S. Cl. ............................ 128/419 P; 128/419 E; 128/419 G
[58] Field of Search ...... 128/419 P, 419 PG, 419 PT, 128/DIG. 25; 604/66

[56] References Cited

U.S. PATENT DOCUMENTS

| | | | |
|---|---|---|---|
| 3,456,134 | 7/1969 | Ko ............................................. 310/8.5 |
| 3,593,718 | 7/1971 | Krasner et al. .................... 128/419 P |
| 3,659,615 | 5/1972 | Enger ................................ 128/419 P |
| 3,777,762 | 12/1973 | Nielsen ................................. 128/419 |
| 3,830,242 | 8/1974 | Greatbatch ....................... 128/419 P |
| 4,009,721 | 3/1977 | Alcidi ............................... 128/419 P |
| 4,041,954 | 8/1977 | Ohara ............................... 128/419 PT |
| 4,077,405 | 3/1978 | Haerten et al. ......................... 604/66 |
| 4,088,138 | 5/1978 | Diack et al. ...................... 128/419 D |
| 4,114,628 | 9/1978 | Rizk ................................ 128/419 PG |
| 4,124,031 | 11/1978 | Mensink et al. ............... 128/419 PT |
| 4,140,132 | 2/1979 | Dahl ................................ 128/419 PG |
| 4,164,944 | 8/1979 | Alley, III et al. ............. 128/419 PG |
| 4,202,339 | 5/1980 | Wirtzfeld et al. ............ 128/419 PG |
| 4,304,238 | 12/1981 | Fischer .......................... 128/419 PG |
| 4,312,354 | 1/1982 | Walters ......................... 128/419 PG |
| 4,421,114 | 12/1984 | Berkovits ..................... 128/419 PG |
| 4,424,812 | 1/1984 | Lesnick ......................... 128/419 PG |
| 4,428,378 | 1/1984 | Anderson et al. ........... 128/419 PG |
| 4,432,363 | 2/1984 | Kakegawa .................... 128/419 PS |
| 4,440,173 | 4/1984 | Hudziak et al. .............. 128/419 PG |
| 4,441,498 | 4/1984 | Nordling .......................... 128/419 P |
| 4,445,512 | 5/1984 | Krupka et al. ............... 128/419 PT |

Primary Examiner—William E. Kamm
Assistant Examiner—Mitchell J. Shein
Attorney, Agent, or Firm—Henry W. Collins; Thomas R. Vigil

[57] ABSTRACT

A piezoelectric device and method are provided for setting or adjusting parameters or functions of an implanted device, such as the pacing rate of a pacer, at the will of its user/wearer or others, simply by making slight impacts on the user/wearer's body near the implanted piezoelectric device. The device has a piezoelectric sensor which picks up the physical impact and converts it to an electrical signal. Additional amplification and detection/decoding circuits can be provided to strengthen the signal and to separate intentional impacts from any unintentional impacts and noise.

20 Claims, 3 Drawing Figures

METHOD AND APPARATUS FOR SETTING AND CHANGING PARAMETERS OR FUNCTIONS OF AN IMPLANTED DEVICE

BACKGROUND OF THE INVENTION

1. Field of the Invention

The present invention relates to a method and apparatus for setting and changing parameters or functions of an implanted device such as a cardiac pacer and more particularly to an apparatus including a peizoelectric device which can be actuated to generate signals for setting and adjusting the implanted device at the will of the wearer or someone else, such as a medical technician.

2. Description of the Prior Art

Heretofore, it has been known to use piezoelectric elements in cardiac pacers such as for energizing a pacer as disclosed in U.S. Pat. No. 3,659,615 or U.S. Pat. No. 3,456,134 and to cause the pacer to vibrate in response to the wearer's activity in an attempt to automatically adjust the pacing rate to the wearer's physical activity, as disclosed in U.S. Pat. No. 4,140,132. Also it has been proposed to utilize a sensor in a pacing lead for sensing blood pressure as disclosed in copending U.S. patent application Ser. No. 632,625, filed July 19, 1985.

Also it has been suggested to use a special element, such as a magnet, for altering a pacing rate or to test the pacer, including its battery, in U.S. Pat. Nos. 4,304,238 and 4,312,354.

Further, it has been suggested to make such changes by use of an ultrasonic radiator operating on an implanted piezoelectric crystal in U.S. Pat. No. 3,777,762.

These prior art devices have generally used the special element (e.g., magnet or ultrasonic radiator) to react with a suitable implanted associate element (e.g., reed switch or piezoelectric crystal) and related circuitry to alter the pacing rate, albeit for increased or decreased pacing or testing. Unfortunately, the wearer may not want to use or will not have the special device, e.g., magnet, with him at all times so that he cannot alter his pacing rate when he wishes.

The automatic type devices, such as disclosed in U.S. Pat. No. 4,140,132 have the disadvantage of having mechanical parts which are less reliable than solid state electronics. Further, the automatic type devices could make rate changes when not desired or fail to make rate changes when desired. For example, assume that the automatic device is implanted in the upper part of the body of the user, near or with the other portions of the pacer. With such an installation, the device becomes sensitive to upper body movement, and is less sensitive to or insensitive to lower body movement. Were the user to bicycle, where there is a great deal of lower body or leg movement, but relatively little upper body movement, the automatic device may not be sensitive enough to cause the desired change in pacing rate to match the increased muscular activity. Were the automatic device's sensitivity increased to compensate, then there is a likelihood that other normal, upper body motions, such as when being bounced about in an automobile on a somewhat bumpy road, would also cause unwanted changes in pacing rate. Clearly, the so-called automatic devices have their drawbacks since it is difficult to make a mechanical automatic type device that will always provide the correct pacing rate. With the apparatus of the present invention one can activate or deactivate an automatic device when the wearer feels it appropriate to do so.

SUMMARY OF THE INVENTION

The method and apparatus of the present invention including a piezoelectric device for setting and adjusting a parameter or function of an implanted device, such as a pacer, eliminate the foregoing disadvantages, as no special element or magnet is required to make a change, and the setting or adjustment is made in a more natural manner by extremely reliable solid state electronics. Further, as a setting or adjustment, such as a change in pacing rate, is made only at the will and discretion of the wearer, there is no tendency to make changes "automatically" when such are not desired. The apparatus comprises and utilizes a piezoelectric sensor implanted in the body of the wearer in such a manner that the wearer can cause, simply on impact, such as by tapping his finger near the sensor, an adjustment, such as of pacing rate. The tapping impact is picked up by the sensor and converted to an electrical signal which can then be used to alter the operation of an implanted device, such as the pacing rate of a pacer, in a manner that is now conventionally done using a special magnet type device disclosed in the aforementioned patents.

The method and apparatus of the present invention may also include amplifying means for strengthening the signal from the piezoelectric sensor and also special decoding means for separating the signal from noise or clutter and/or to use a plurality of different signals to carry out more than one function. In such case, the wearer might make a sequence of taps and the decoding means then separate out the taps into various coded signals, each being differently utilized to perform a desired function, such as to raise or lower the pacing rate of a pacer or to test a portion of a device.

The method and apparatus of the present invention are particularly useful for setting and adjusting the pacing rate of a pacer, provide a convenient, always available, and natural way to do so simply by tapping out, such as with a finger on the wearer's body, a rhythmic sequence. The tapping is then detected by the piezoelectric sensor, if need be amplified by the amplifying means, decoded by the decoding means, and then used to alter the pacer's circuitry to provide a desired different pacing rate or test or other function.

DESCRIPTION OF THE PREFERRED EMBODIMENT

Figure 1:
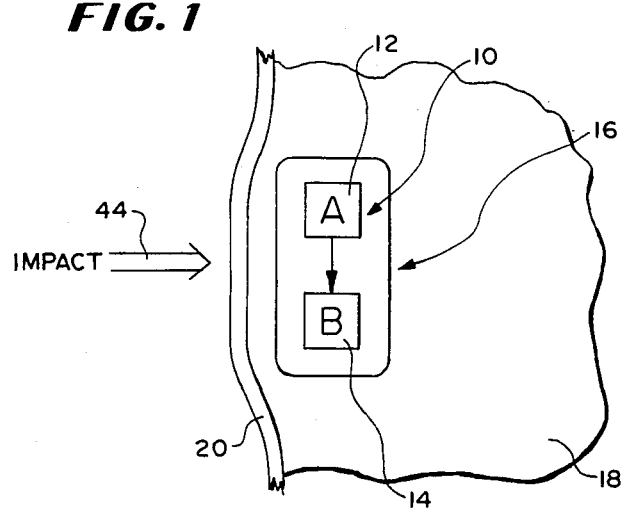
FIG. 1 is a block circuit diagram of the apparatus of the present invention including a piezoelectric device and shows the apparatus implanted in a human body.

Referring now to FIG. 1 there is illustrated therein a block circuit diagram of the apparatus of the present invention which is generally identified by reference numeral 10. The apparatus 10 includes a piezoelectric sensor "A" also identified by reference numeral 12, and signal processing circuitry "B" also identified by reference numeral 14, all of which are enclosed within a conventional, implantable cardiac pacer electronic module 16. The entire module 16, including an associated battery (not shown) for powering the same, is implanted within a body 18 of the user or wearer, underneath his/her skin 20. An ideal location for such an implant is in the upper chest area or in the abdominal wall.

Figure 2:
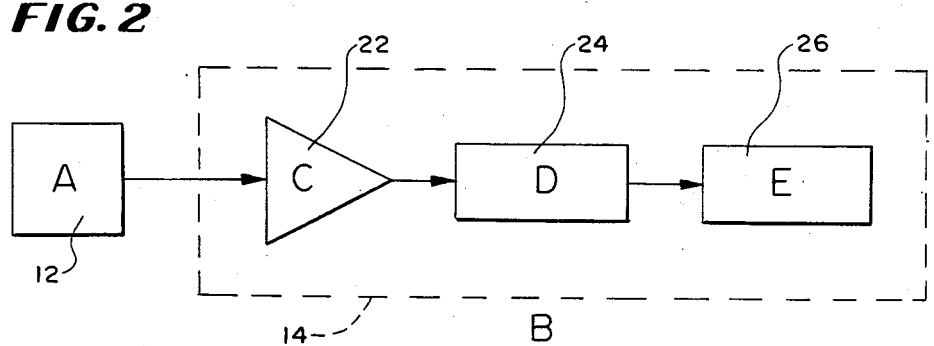
FIG. 2 is an expanded block circuit diagram of the apparatus of the present invention shown in FIG. 1.

Referring now to FIG. 2, the signal processing circuitry "B" preferably comprises an amplifying circuit "C" also identified by the reference numeral 22 for amplifying the strength of the signal from the piezoelectric sensor "A". Such amplifying circuit "C" may also act to filter the voltage signal from the piezoelectric sensor "A".

In one preferred embodiment, the amplified voltage signal from the amplifying circuit "C" is fed to a detection or decoding circuit "D" also identified by reference numeral 24, for testing or determining that the signal from the piezoelectric sensor "A" and amplifying circuit "C" are the proper signal/value to set or adjust the pacing rate. The decoder or detection circuit "D" then outputs to a pacing rate setting or adjusting circuit "E" also identified by the reference numeral 26, which actually sets or adjusts the pacing rate of the pacer in accordance with the value of the signal inputted from the decoding or detection circuit "D".

The specific construction of circuits "D" and "E" depends upon the complexity of the commands which the pacer 16 is to respond to in setting and adjusting the pacing rate. However, these circuits "D" and "E" are generally well known and conventional, and are of a type similar to that shown in the above described prior art patents, such as, for example, in U.S. Pat. Nos. 4,140,132 and 4,312,354. A person skilled in the art of cardiac pacer electronics can easily build the necessary detection circuit "D" and rate changing circuitry "E" for the various commands and codes desired, preferably with solid state digital electronics.

Figure 3:
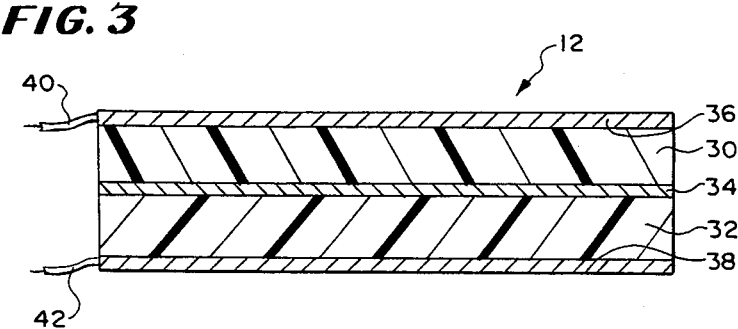
FIG. 3 is a cross-sectional view of one piezoelectric sensor that can be used in the apparatus shown in FIG. 1.

Various piezoelectric technology can be utilized to build the sensor "A" including polymeric ferroelectric or polymer polyvinylidene fluoride film type construction. However, in this instance, the piezoelectric sensor "A" is more like the type described in copending U.S. patent application Ser. No. 632,625, filed July 19, 1984, As illustrated in FIG. 3, the piezoelectric sensor "A" is of the bimorph type construction and has two sheets 30 and 32 of ceramic material separated by a skin 34, of, for example, brass. The two ceramic sheets 30 and 32 can be selected from the following: barium titanate, lead titanate zirconate, lead metaniobate, and/or sodium bismuth titanate. As shown, two outer surfaces 36 and 38 of the sensor 12 are composed of fired on silver or electroless nickel to which a pair of wires 40 and 42 are secured. Bimorphs of this type are manufactured by Piezoelectric Products, Inc. and by Vernitron Piezoelectric Division.

It is understood that the wires 40 and 42 are connected to the amplifying circuit "C" in a known and conventional manner.

In the operation of the apparatus 10, to adjust or set the pacing rate, an impact, represented by the arrow 44 is imposed upon the body of the wearer/user. Depending on the sensitivity of the piezoelectric sensor 12 and its placement in the body 18 and closeness to the skin 20, the impact required could be slight or significant. A slight impact could be that of a left hand finger tapped on the chest near the sensor 12. The piezoelectric sensor 12 picks up the tapping impact and converts it into an electrical signal, such as a voltage spike, which in turn is amplified in magnitude by the amplifying circuit 22. The amplifying circuit 22 outputs to the detection or decoding circuit 24, which then determines whether the impacts are in the correct sequence and rhythm to cause the detection circuit 24 to output to the pacer rate adjusting and setting circuit 26. If the impacts are correctly coded, the detection or decoding circuit 24 will give the necessary signals to set, raise or lower the pacing rate. If the impacts are not in the correct sequence, of course, nothing happens. If desired, the detection, decoding circuits and the rate setting and adjusting circuit can respond to one coded sequence of impacts to set the pacing rate; a second coded sequence of impacts to lower the rate; a third coded sequence to raise the rate; a fourth coded sequence to test the pacer and/or its battery, etc. The use of the sequenced impacts and decoding circuit completely eliminate the possibility of noise or random impacts causing any unwanted change.

From the foregoing, it is apparent that with the method and apparatus of the present invention, the pacing rate of a cardiac pacer can be easily and quickly set or adjusted by the user/wearer simply by impacting his body near the piezoelectric sensor 12. Of course, others, such as medical technicians or doctors, could also test, set or adjust the pacer or its battery and rate by impacting the user/wearer's body in a similar manner. All this setting and adjustment is done without the need for a special magnet, or even more cumbersome ultrasonic or other device. However, if it were desired to permit the user to perform only certain functions, but have the medical technician capable of performing other functions, either special codes could be provided only to the technician or that portion made operable only by a special element such as the prior art magnet.

It is to be understood that although the method and apparatus of the present invention have been described with respect to their particular utility in a pacing system, such method and apparatus also can be used in prostheses, drug delivery systems, neural stimulators, etc.

While only one preferred embodiment of the apparatus 10 and method for setting and adjusting the pacing rate have been illustrated and described, from the foregoing, it will be understood that variations, modifications and equivalent structures and use thereof can be made to the apparatus 10 without departing from the teachings of the present invention. Accordingly, the scope of the invention is only to be limited as necessitated by the accompanying claims.

I claim:

1. A method for setting and adjusting parameters or functions of an implanted device utilizing a piezoelectric sensor implanted in the user's body, comprising the steps of:
   a. causing a physical impact on the user's body adjacent the sensor;
   b. piezoelectrically converting the impact into an appropriate electrical signal; and
   c. utilizing the electrical signal for setting and/or adjusting parameters or functions of the implanted device, whereby the parameters or functions can be set or adjusted at will by simply causing a physical impact on the user's body adjacent the sensor.

2. The method of claim 1 comprising the step of amplifying the electrical signal prior to utilizing the same to set or adjust the parameter or function.

3. The method of claim 1 comprising the step of decoding the electrical signal prior to utilizing the same to set or adjust the parameter or function, whereby the effects of noise and unintentional impacts are eliminated.

4. The method of claim 3 comprising the steps of causing a sequenced plurality of physical impacts as called for in step a, converting the sequenced impacts into an appropriate sequence of electrical signals as called for in step b, and decoding the sequence of electrical signals to the electrical signal utilized in step c.

5. The method of claim 4 used in controlling a pacer and comprising the step of programming one sequence of physical impacts for increasing the pacing rate.

6. The method of claim 4 used in a pacer system and comprising the step of programming one sequence of physical impacts for decreasing the pacing rate.

7. The method of claim 4 used in a pacer system and comprising the step of programming one sequence of physical impacts for testing the pacer and/or a battery in the pacer of the pacer system.

8. The method of claim 4 used in a pacer system and comprising the steps of:
   a. programming one sequence of physical impacts for increasing the pacing rate,
   b. programming a second sequence of physical impacts for decreasing the pacing rate, and
   c. programming a third sequence of physical impacts for testing the pacer.

9. The method of claim 8 comprising the step of programming a fourth sequence of physical impacts for testing the battery.

10. Piezoelectric sensor means for setting and adjusting the parameters or functions of an implantable device, said sensor means comprising an electrical circuit coupled to the implantable device and a piezoelectric sensor implantable in the body of the user and connected to said electrical circuit, said piezoelectric sensor means including means for converting physical impacts on the body of the user adjacent said sensor into electrical signals which are supplied to an utilized by said electrical circuit for setting or adjusting parameters or functions of the implantable device, whereby the operation of the implantable device can be set or adjusted by a simple impact on the body of the user adjacent said sensor.

11. The sensor means of claim 10 further comprising amplifying means for amplifying the signal from said piezoelectric sensor before transmitting the amplified signal to said electrical circuit.

12. The device of claim 9 further comprising decoding means for decoding the electrical signals from said piezoelectric sensor into a signal to be utilized by said electrical circuit.

13. The sensor means of claim 11 further comprising decoding means for decoding electrical signals from said amplifying means into a signal to be utilized by said electrical circuit.

14. The sensor means of claim 10 wherein said piezoelectric sensor comprises a bimorph.

15. The sensor means of claim 14 wherein said bimorph consists of at least two sheets of one of the following : barium titanate, lead titanate zirconate, lead metaniobate and sodium titanate, separated by a shim.

16. The sensor means of claim 15 wherein one of said sheets is connected to amplifying means for increasing the signal from said bimorph.

17. The sensor means of claim 16 wherein said amplifying means are connected to decoding means for eliminating the unwanted changes of pacing rate in response to noise, and said decoding means are connected to said electrical circuit for setting and/or altering the parameters of the implanted device.

18. The device of claim 9 wherein said piezoelectric sensor is of the polymeric ferroelectric type.

19. The sensor means of claim 10 wherein said piezoelectric sensor utilizes a polymer polyvinylidene fluoride film construction.

20. The device of claim 10 wherein said implanted device is a cardiac pacer.

* * * * *